(12) United States Patent
Battefeld et al.

(10) Patent No.: US 9,784,669 B2
(45) Date of Patent: Oct. 10, 2017

(54) NEPHELOMETRIC TURBIDIMETER

(71) Applicant: HACH LANGE GMBH, Berlin (DE)

(72) Inventors: Manfred Battefeld, Duesseldorf (DE);
Bas De Heij, Dormagen (DE);
Hans-Joachim Kumpch, Berlin (DE);
Andreas Mitreiter, Kleinmachnow
(DE); Andreas Golitz, Moers (DE)

(*) Notice: Subject to any disclaimer, the term of this patent is extended or adjusted under 35 U.S.C. 154(b) by 0 days.

(21) Appl. No.: 14/951,504

(22) Filed: Nov. 25, 2015

(65) Prior Publication Data
US 2016/0153891 A1  Jun. 2, 2016

(30) Foreign Application Priority Data

Nov. 27, 2014  (EP) .................................... 14195059

(51) Int. Cl.
*G01N 1/10* (2006.01)
*G01N 21/03* (2006.01)
*G01N 21/51* (2006.01)
*G01N 21/49* (2006.01)

(52) U.S. Cl.
CPC ......... *G01N 21/0303* (2013.01); *G01N 21/49* (2013.01); *G01N 21/51* (2013.01); *G01N 2021/513* (2013.01); *G01N 2201/064* (2013.01); *G01N 2201/068* (2013.01)

(58) Field of Classification Search
CPC ...... G01N 21/49; G01N 21/05; G01N 21/532; G01N 21/47; G01N 21/4785; G01N 21/53; G01N 21/15; G01N 21/0303; G01N 21/51; G01N 2021/513; G01N 2021/4726; G01N 2201/068; G01N 2201/064; G01N 2201/0227

USPC ................ 356/244, 246, 432–440, 335–343; 422/512, 546, 550, 560
See application file for complete search history.

(56) References Cited

U.S. PATENT DOCUMENTS

| | | | | |
|---|---|---|---|---|
| 4,250,394 | A | * | 2/1981 | O'Connor ........ G01N 33/54313 250/574 |
| 4,512,735 | A | * | 4/1985 | Nilsson ............... B29C 49/0073 425/526 |
| 4,678,326 | A | * | 7/1987 | Harjunmaa .......... G01N 21/255 250/227.11 |
| 5,906,772 | A | * | 5/1999 | Patterson ........... G01N 21/4785 252/408.1 |
| 8,724,107 | B2 | | 5/2014 | Palumbo |

(Continued)

FOREIGN PATENT DOCUMENTS

| | | |
|---|---|---|
| EP | 1 909 094 A1 | 4/2008 |
| WO | WO 2011/038769 A1 | 4/2011 |

*Primary Examiner* — Hoa Pham
(74) *Attorney, Agent, or Firm* — Patent Law Offices of Dr. Norman B. Thot

(57) ABSTRACT

A nephelometric turbidimeter with a cylindrical turbidimeter vial. The cylindrical turbidimeter vial includes a transparent vial body and a circular optical shielding configured to optically block an inside from an outside of the turbidimeter vial. The vial body comprises a transparent and flat bottom inlet window, and a transparent vial cylinder body. The vial cylinder body comprises a circular outlet window. The optical shielding is arranged axially above the outlet window of the vial cylinder body, over a part of an axial length of the vial cylinder body, and axially adjacent to a non-shielded part of the vial cylinder body which serves as the outlet window.

11 Claims, 6 Drawing Sheets

(56) References Cited

U.S. PATENT DOCUMENTS

| | | | |
|---|---|---|---|
| 2005/0254055 A1* | 11/2005 | Peng | C12M 41/36 |
| | | | 356/432 |
| 2008/0072664 A1 | 3/2008 | Hansen et al. | |
| 2008/0123091 A1 | 5/2008 | Yamamoto et al. | |
| 2009/0272750 A1* | 11/2009 | Rajagopalan | B65D 1/0276 |
| | | | 220/600 |
| 2012/0140230 A1 | 6/2012 | Miller | |
| 2012/0244628 A1 | 9/2012 | Rueeck et al. | |
| 2016/0153886 A1* | 6/2016 | De Heij | G01N 21/05 |
| | | | 356/339 |
| 2016/0153893 A1* | 6/2016 | Battefeld | G01N 21/51 |
| | | | 356/246 |

\* cited by examiner

NEPHELOMETRIC TURBIDIMETER

CROSS REFERENCE TO PRIOR APPLICATIONS

Priority is claimed to European Patent Application No. EP 14195059.2, filed Nov. 27, 2014. The entire disclosure of said application is incorporated by reference herein.

FIELD

The present invention relates to a nephelometric laboratory or process turbidimeter to measure the turbidity of a fluid sample, for example, of drinking water, in a transparent sample vial.

BACKGROUND

A nephelometric turbidimeter determines the concentration of solid or other particles suspended in a fluid, which can generally be a liquid, a gas, or a mixture of liquid and gas. U.S. Pat. No. 8,724,107 B2 describes a nephelometric turbidimeter with a cylindrical turbidimeter vial comprising a transparent and flat bottom inlet window through which a measurement light beam axially enters the vial interior. An axial middle section of the vial cylinder body defines a transparent outlet window through which the light scattered by the suspended solid particles radially exits the vial interior. The cylindrical outlet window is radially surrounded by an annular light collecting means which optically cooperates with a light sensor which detects the scattered and collected light. The primary light signal, which is only caused by the light scattered within the relevant fluid volume, is relatively small so that any disturbing light causing a secondary signal should, if possible, be avoided.

The vial body is provided with a cylindrical optical shielding at the cylinder body, the shielding being axially located between the bottom inlet window and the circular outlet window. This shielding provides that light scattered by a particle layer at the bottom inlet window of the vial cannot directly irradiate the light collecting means. No shielding is provided in the upper portion of the vial axially beyond the circular outlet window because the scattered light coming from the bottom inlet window is totally reflected by and at the boundary between the vial body and the surrounding atmosphere.

The vial body has a top opening which is closed by a vial cap which can be a part of the turbidimeter to provide a fluid-tight vial interior. The measurement light beam can be reflected downwardly at an interior wall of the vial cap, and can thereby be directed directly or indirectly to the light collecting means and/or the optical turbidity sensor, and can thereby generate a secondary signal. The vial in a laboratory turbidimeter is normally not completely filled with a liquid sample so that the measurement light beam can also be reflected downwardly at the boundary layer of liquid and air.

In drinking water applications, the measurement light beam's intensity is only minimally reduced by scattering in the fluid sample so that the reflected measurement beam causes secondary signals being many times more intense than the primary signal.

The vial in a laboratory turbidimeter is exchanged for every measurement, so that the vial is manually taken out of a vial chamber of the turbidimeter. If the vial is put down on a hard surface, the outside of the bottom inlet window can be scratched by the hard surface. A scratch can cause strong optical fractions of the measurement light beam passing the scratch at the bottom inlet window, thereby causing intense secondary signals.

Since the vial is exchanged manually in a laboratory turbidimeter, fingerprints causing optical fraction and scattering also cannot be avoided. The fingerprints can thereby also cause secondary signals and falsify the result of the turbidity measurement.

SUMMARY

An aspect of the present invention is to provide a nephelometric turbidimeter, and in particular to provide a turbidimeter vial which avoids secondary signals.

In an embodiment, the present invention provides a nephelometric turbidimeter with a cylindrical turbidimeter vial. The cylindrical turbidimeter vial includes a vial body which is transparent, and an optical shielding which is circular and optically blocks an inside from an outside of the turbidimeter vial. The vial body comprises a bottom inlet window configured to be transparent and flat, and a vial cylinder body configured to be transparent. The vial cylinder body comprises an outlet window configured to be circular. The optical shielding is arranged axially above the outlet window of the vial cylinder body, over a part of an axial length of the vial cylinder body, and axially adjacent to a non-shielded part of the vial cylinder body which serves as the outlet window.

BRIEF DESCRIPTION OF THE DRAWINGS

The present invention is described in greater detail below on the basis of embodiments and of the drawings in which.

DETAILED DESCRIPTION

Figure 1:
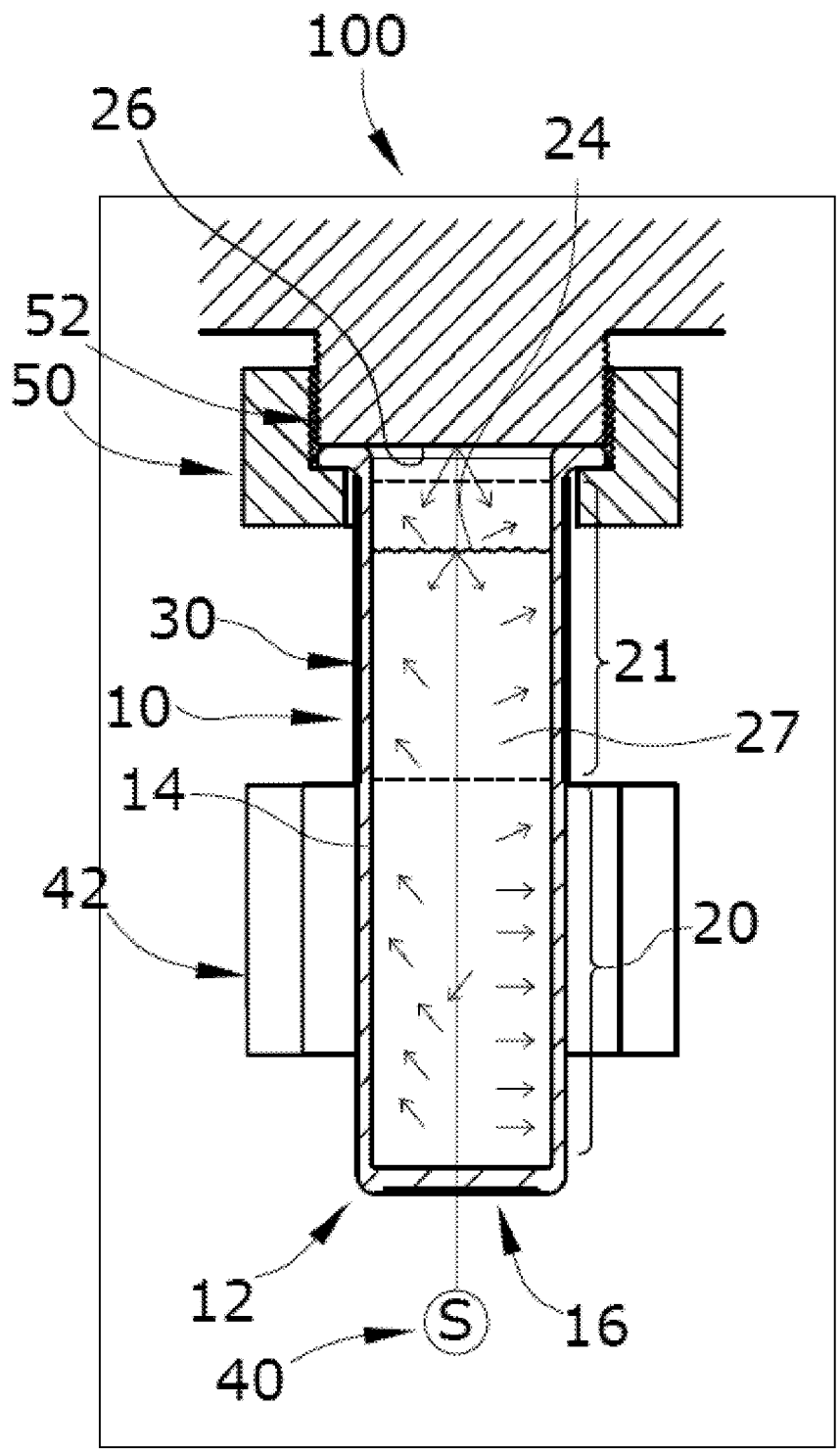
FIG. 1 shows schematically a nephelometric turbidimeter with a vial being fixed in a vial chamber of the turbidimeter.

In an embodiment, the present invention provides a nephelometric turbidimeter with a cylindrical turbidimeter vial and with a measurement light source generating a measurement light beam. The measurement light beam is axially directed into the vial interior through a flat and plane bottom inlet window of the vial body. The light source generates suitable electromagnetic radiation which can be of any suitable wavelength. The turbidimeter is also provided with a scattering light detecting arrangement to receive and detect the light scattered by particles suspended in the fluid sample, and being scattered in a more or less right angle with respect to the longitudinal orientation of the measurement light beam.

The vial comprises a transparent cylinder body with a circular outlet window which is axially aligned with the light detecting arrangement. The vial is provided with a cylindrical optical shielding at the cylinder body axially above the outlet window of the cylinder body. The shielding can be provided axially adjacent to the non-shielded portion of the vial body which serves as the outlet window. The shielding can axially extend from the top edge of the circular outlet window to the top end of the vial body so that the complete top portion above the circular outlet window is shielded.

If the measurement light beam is reflected downwardly by a liquid surface or by a surface of the vial cap downwardly into the vial interior, the reflected light beam cannot leave the vial in the shielded top portion of the vial. A direct irradiation by the reflected light beam of any part of the light detecting arrangement can thereby be excluded. In the lower part of the vial body, the reflected light beam is, due to an acute reflection angle, totally reflected and thereby directed downwardly to the inlet window through which the reflected light beam leaves the vial. The provision of the optical shielding at the top portion of the vial body above the circular outlet window is particularly useful in drinking water applications because the turbidity-caused weakening of the measurement light beam can be very low, so that the reflected measurement light beam still can have high intensity.

In an embodiment of the present invention, the shielding can, for example, be provided with a light-absorbing structure at the proximal shielding side. The light-absorbing structure absorbs most of the energy of the impinging measurement light beam so that the thereby weakened reflected measurement light beam has a significantly reduced intensity when traveling further downwards through the vial.

In an embodiment of the present invention, the shielding can, for example, be provided by a shielding sheet which is attached to the outside of the transparent vial body. The shielding sheet can be glued to the outside surface of the transparent vial body. The shielding sheet motivates the user to touch the vial body at the shielded area so that fingerprints at the circular outlet window and at the bottom inlet window are avoided. The shielding sheet can be printed with written information or with a pictogram to make clear to the user that the vial should only be touched at the shielding portion.

In an embodiment of the present invention, the shielding is provided over at least 270° of the circumference of the vial body, but is not provided over the complete circumference of the vial body, so that a control window is defined by the non-shielded area. In case a shielding sheet is provided at the outside of the transparent vial body, the circumference of the shielding sheet is some millimeters less than the outside circumference of the vial cylinder body so that the circumferential edges of the shielding sheet cannot overlap, and thereby cannot create a local radial elevation which could cause a non-parallel alignment of the vial with the measurement light beam.

The control window allows, in particular in a laboratory application, a visual control of the level of a sample liquid within the vial. The correct level of the sample liquid within the vial is important to make sure that the level of the sample liquid is vertically not too low and not too close to the circular outlet window to avoid reflections of the measurement light beam at the boundary-layer which could directly irradiate the measurement light detecting device.

In an embodiment of the present invention, the shielding can, for example, be provided at least in the upper third of the vertical extent of the vial body.

In an embodiment of the present invention, the light inlet window can, for example, be surrounded by one or more axial spacing elements. The axial spacing elements can, for example, be defined by three or more small vertical feet knobs which keep the inlet window vertically spaced apart from a surface on which the vial is standing on. The axial spacing elements avoid a scratching of the inlet window when the vial body is vertically set down on a ground surface which might be hard or covered with hard particles. This aspect of the present invention is generally not limited to a vial body with an optical shielding, but can also be provided to a vial body without an optical shielding.

In an embodiment of the present invention, the axial spacing element is provided by a circular bulge surrounding the inlet window so that the space enclosed by the inlet window, the circular bulge, and the ground surface, is substantially closed. When the vertically orientated vial is standing on a horizontal surface, the inlet window is thereby protected against dust, powder etc. of the environment.

The vial is provided with an opening at the top of the vial body. According to another embodiment of the present invention, the vial opening can, for example, be surrounded by a circular flange defining a flange ring projecting radially outwardly from the vial cylinder body. The circular flange serves as a fixation structure for fixing a vial cap or for closing and fixing the vial in a vial chamber of the turbidimeter.

In an embodiment of the present invention, the axial thickness of the vial flange can, for example, be larger than the radial thickness of the vial cylinder body. The vial body is generally made out of glass and is formed out of a tube material. The flange of a state-of-the-art vial therefore is normally axially not thicker than the radial thickness of the vial cylinder body. In a laboratory turbidimeter, the vial body is fixed to a turbidimeter-sided vial holder by a clamping ring which axially clamps the circular fixation flange against a corresponding portion of the turbidimeter.

The thickness of the circular clamping flange can be increased by double-folding the vial body material in the flange area so that the axial thickness of the flange can be increased significantly and can be almost doubled. The clamping force can be increased accordingly so that a liquid-tight fixation of the vial body in and at the turbidimeter can be realized without the risk of breaking the circular fixation flange.

In an embodiment of the present invention, the material of the inlet window can, for example, be different from the material of the vial cylinder body. Both materials can be selected to perfectly match with the mechanical and physical requirement for the respective vial portion. The window body of the inlet window and the transparent cylinder body can be melted together at their respective edge portions.

One embodiment of the present invention is described below with reference to the drawings.

FIG. 1 shows schematically a nephelometric turbidimeter 100 for determination of the turbidity in a fluid sample 27, preferably in a liquid sample 27. The present nephelometric turbidimeter 100 is a laboratory turbidimeter so that the turbidimeter vial 10 is changed for every turbidity measurement. The nephelometric turbidimeter 100 is provided with a turbidimeter vial 10 which is cylindrical, a measurement light source 40 and a scattering light detecting arrangement 42. The turbidimeter vial 10 is orientated verticality, but can generally also be orientated with another orientation. All spatial terms refer to a vertical orientation as shown in FIG. 1.

The measurement light source 40 generates a measurement light beam 41 which can be a light beam of any suitable kind of electromagnetic radiation. The measurement light beam 41 axially enters the vial interior through an inlet window 16 of the vial 10. The measurement light beam 41 is scattered by solid particles dispersed in the liquid sample 27, and the scattered light is detected by the scattering light detecting arrangement 42. The scattering light detecting arrangement 42 can consist of an annular optical reflection device and a light sensor which is sensible for the electromagnetic radiation generated by the measurement light source 40.

The turbidimeter vial 10 is defined by vial body 12 with a vial cylinder body 14 made out of transparent glass, an inlet window body 15 defining the bottom wall of the turbidimeter vial 10, and a circular flange 18 around the top vial opening 13. The inlet window body 15 defines the inlet window 16 and may be made of which is glass different from the glass of the vial cylinder body 14. The turbidimeter vial 10 has a longitudinal vial axis 11 which is coaxially in-line with the measurement light beam 41.

Figure 2:
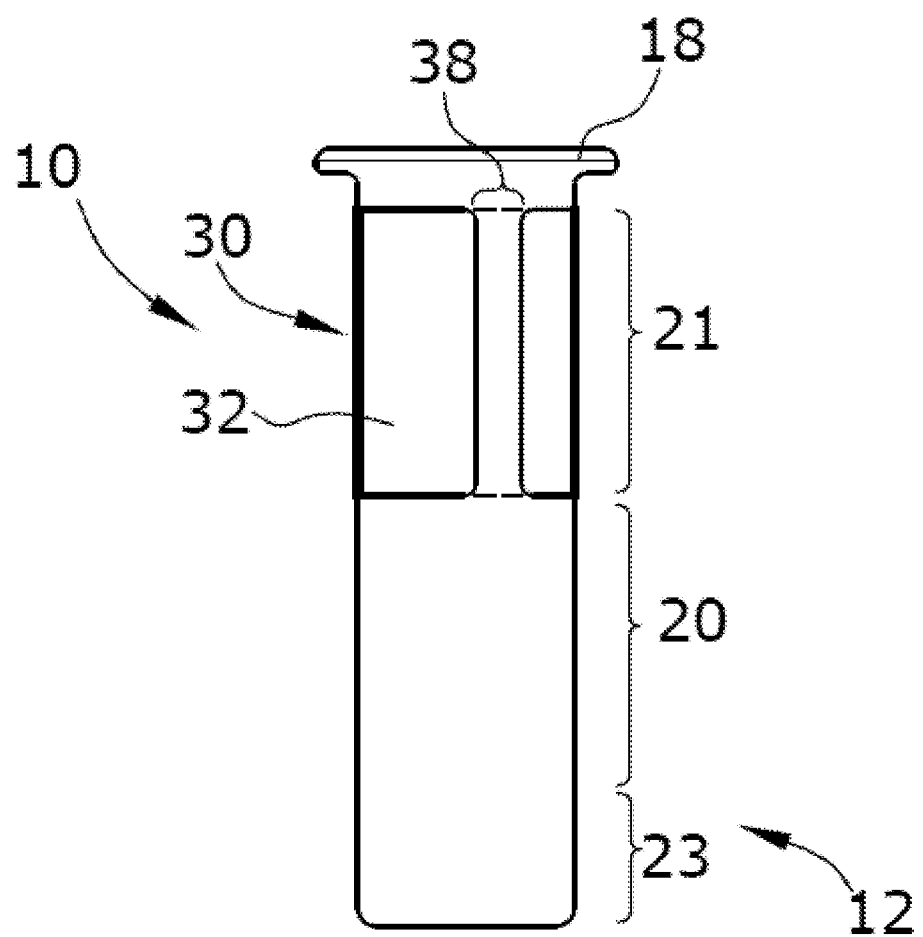
FIG. 2 shows a lateral view of the vial of the turbidimeter of FIG. 1.
Figure 3:
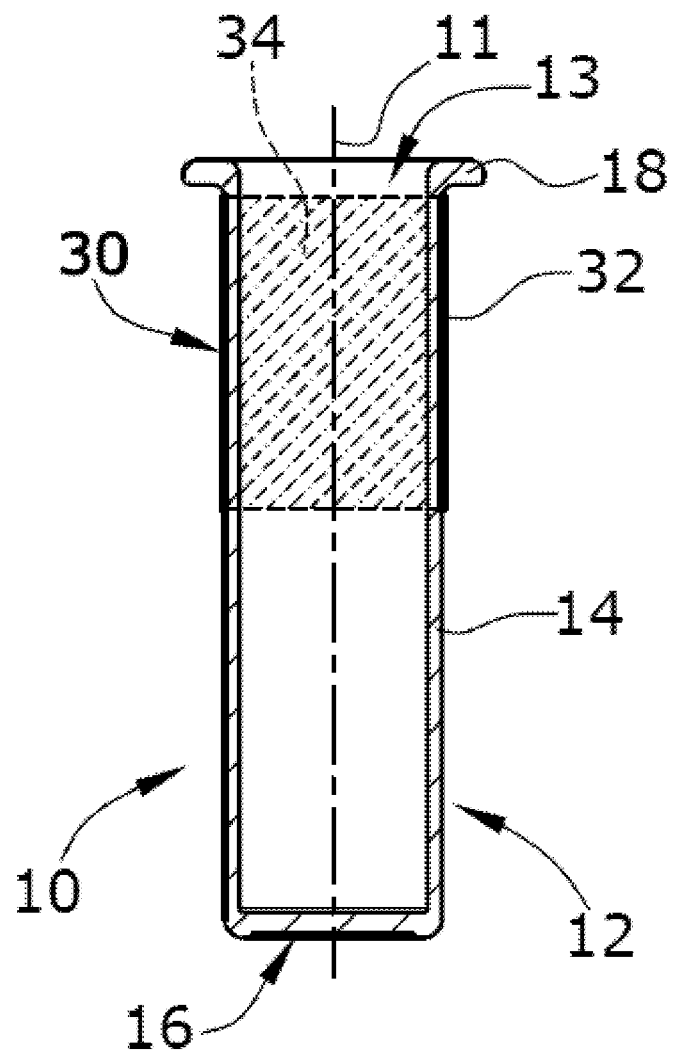
FIG. 3 shows a longitudinal cross-section of the vial of FIG. 2.

The turbidimeter vial 10 is, seen in vertical direction, separated into three vertical portions 23,20,21, namely the bottom portion 23, the outlet window 20 and the top portion 21, as shown in FIG. 2. The top portion 21 is provided with a cylindrical optical shielding 30. The outlet window 20 is circular and transparent for the scattering light and is axially aligned with the scattering light detecting arrangement 42. The bottom portion 23 is not shielded but can generally also be shielded.

The circular optical shielding 30 at the top portion 21 is provided by a shielding sheet 32 which is attached by gluing to the outside surface of the vial body 12. The inside surface of the shielding sheet 32 is provided with a black-colored and light-absorbing structure 34 which absorbs most of the impinging light resulting from reflections of the measurement light beam 41. As that can best be seen in FIG. 2, the shielding sheet 32 is not provided over the complete circumference of the vial body 12, but over about 350°, so that the circumferential edges of the shielding sheet 32 leave a control window 38 open between them. The control window 38 allows for a visual monitoring of the filling level of the liquid sample 27 in the turbidimeter vial 10 laterally from the outside of the turbidimeter vial 10. The shielding sheet 32 may be provided with printed information 36.

Figure 4:
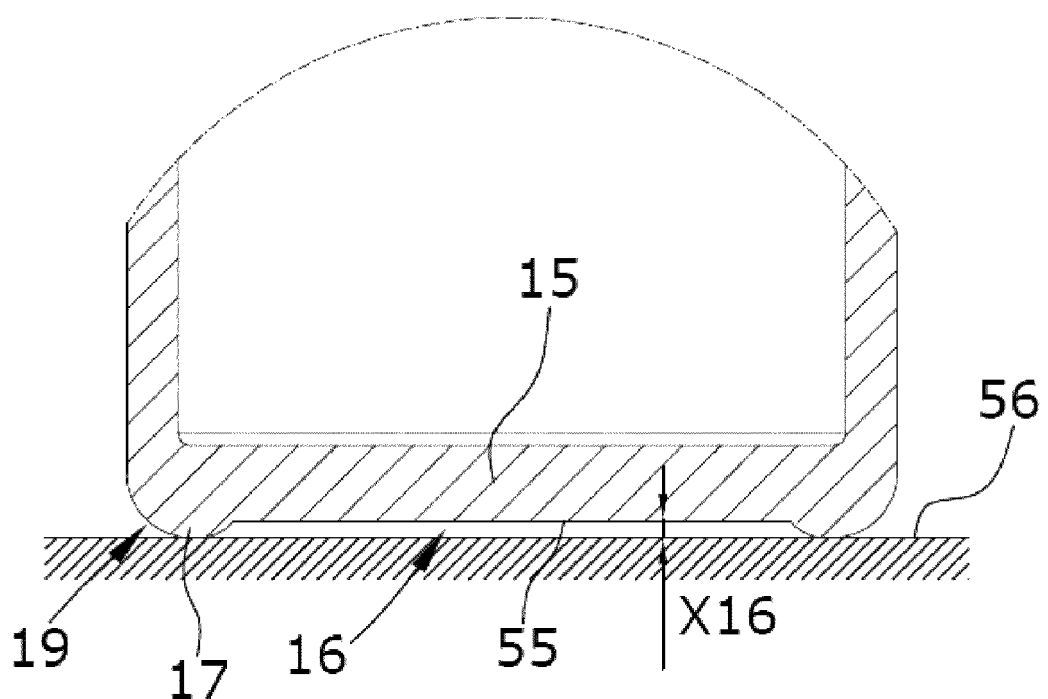
FIG. 4 shows an enlarged view of the inlet window of the vial of FIG. 3.

As can best be seen in FIG. 4, the inlet window body 15 is protected against scratching by an axial spacing element 19 defined by a circular bulge 17 surrounding the inlet window 16. The outside surface 55 of the inlet window body 15 is vertically displaced from a horizontal ground surface 56 with an axial displacement which is identical with the vertical spacing element extension X16 of 0.4 mm to 1.5 mm.

Figure 5:
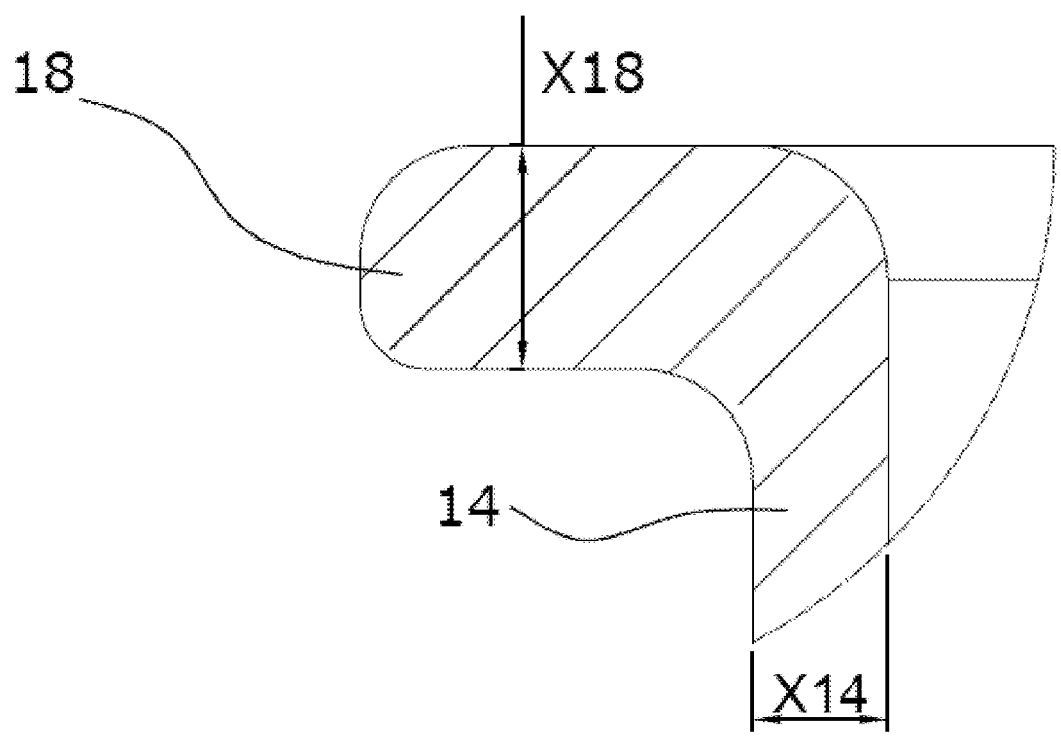
FIG. 5 shows an enlarged view of the circular flange of the vial of FIG. 3.
Figure 6:
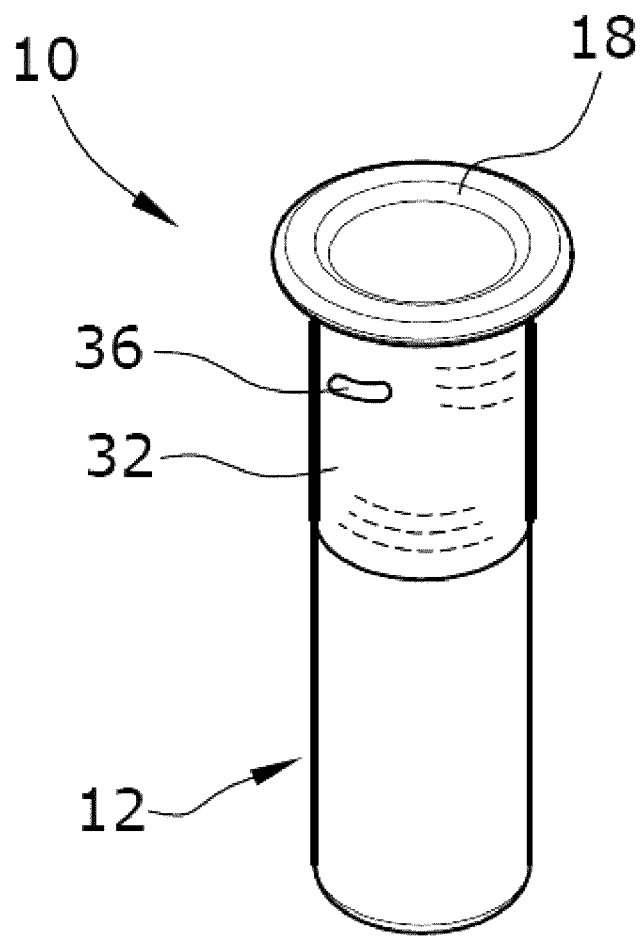
FIG. 6 shows a perspective view of the vial of FIG. 2.

As can best be seen in FIG. 5, the circular flange 18 has an axial thickness X18 which is about 170% of the radial thickness X14 of the vial cylinder body 14.

As can be seen in FIG. 1, the turbidimeter vial 10 is fixed in a vial chamber of the nephelometric turbidimeter 100 by a threaded clamping ring 50 which is fixed to a threaded fixation portion 52, thereby defining a vial cap or vial cover. The threaded fixation portion 52 defines a horizontal top wall 26 of the vial interior.

The measurement light beam 41 generated by the measurement light source 40 axially enters the vial interior through the inlet window 16. The measurement light beam 41 is scattered by particles dispersed in the liquid sample 27. If the liquid sample 27 is drinking water, only a very small fraction of the light beam's intensity is scattered. The scattered light leaving the turbidimeter vial 10 horizontally through the outlet window 20 is received by the scattering light detecting arrangement 42. The remaining measurement light beam 41 is reflected at the liquid surface 24 and at the horizontal top wall 26 so that a relatively high fraction of the light beam's intensity is reflected downwardly. The cylindrical optical shielding 30 at the top portion 23 of the turbidimeter vial 10 avoids that the reflected measurement light beam can directly irradiate the scattering light detecting arrangement 42.

The present invention is not limited to embodiments described herein; reference should be had to the appended claims.

What is claimed is:

1. A nephelometric turbidimeter with a cylindrical turbidimeter vial, the cylindrical turbidimeter vial comprising:
   a vial body configured to be transparent, the vial body comprising,
      a bottom inlet window configured to be transparent, the bottom inlet window comprising a top surface and a bottom surface which are each configured to be flat and parallel with respect to each other, and
      a vial cylinder body configured to be transparent, the vial cylinder body comprising an outlet window configured to be circular; and
   an optical shielding configured to be circular and to optically block an inside from an outside of the turbidimeter vial, the optical shielding being arranged,
      axially above the outlet window of the vial cylinder body,
      over a part of an axial length of the vial cylinder body,
      axially adjacent to a non-shielded part of the vial cylinder body which serves as the outlet window, and
      over at least 270° of a circumference of the vial body and not over a complete circumference of the vial body so that a control window is defined by a non-shielded area.

2. The nephelometric turbidimeter as recited in claim 1, wherein the optical shielding comprises a light-absorbing structure arranged at a proximal shielding side.

3. The nephelometric turbidimeter as recited in claim 1, wherein the optical shielding (30) comprises a shielding sheet which is attached to an outside of the vial body.

4. The nephelometric turbidimeter as recited in claim 1, wherein the optical shielding is arranged at least in an upper third of the vial body.

5. The nephelometric turbidimeter as recited in claim 1, wherein the bottom inlet window is surrounded by at least one axial spacing element.

6. The nephelometric turbidimeter as recited in claim 5, wherein the at least one axial spacing element is provided by a circular bulge which surrounds the bottom inlet window.

7. The nephelometric turbidimeter as recited in claim 1, wherein,
   the turbidimeter vial further comprises a circular flange and an opening,
   the opening is arranged at a top of the vial body, and
   the opening is surrounded by the circular flange.

8. The nephelometric turbidimeter as recited in claim 7, wherein,
   the circular flange comprises an axial thickness,
   the vial cylinder body comprises a radial thickness, and
   the axial thickness of the circular flange is larger than the radial thickness of the vial cylinder body.

9. The nephelometric turbidimeter as recited in claim 1, wherein
   the bottom inlet window comprises a window body which is made of a first material,
   the vial cylinder body is made of a second material, and
   the first material is different from the second material.

10. A cylindrical turbidimeter vial for a nephelometric turbidimeter, the vial comprising:
    a vial body configured to be transparent, the vial body comprising, a bottom inlet window configured to be transparent, the bottom inlet window comprising a top surface and a bottom surface which are each configured to be flat and parallel with respect to each other, and a vial cylinder body configured to be transparent, the vial cylinder body comprising an outlet window configured to be circular; and an optical shielding configured to be circular and to optically block an inside from an outside of the turbidimeter vial, the optical shielding being arranged, axially above the outlet window of the vial cylinder body, over a part of an axial length of the vial cylinder body, axially adjacent to a non-shielded part of the vial cylinder body which serves as the outlet window, and over at least 270° of a circumference of the vial body and not over a complete circumference of the vial body so that a control window is defined by a non-shielded area.

11. A cylindrical turbidimeter vial for a nephelometric turbidimeter, the vial comprising:

a vial body configured to be transparent, the vial body comprising, a bottom inlet window configured to be transparent, the bottom inlet window comprising a top surface and a bottom surface which are each configured to be flat and parallel with respect to each other, and a vial cylinder body configured to be transparent, the vial cylinder body comprising an outlet window configured to be circular; and an optical shielding configured to be circular and to optically block an inside from an outside of the turbidimeter vial, the optical shielding being arranged, axially above the outlet window of the vial cylinder body, over a part of an axial length of the vial cylinder body, axially adjacent to a non-shielded part of the vial cylinder body which serves as the outlet window, and over at least 270° of a circumference of the vial body and not over a complete circumference of the glass vial body so that a control window is defined by a non-shielded area, wherein, the bottom inlet window is surrounded by at least one axial spacing element, and the at least one axial spacing element is provided by a circular bulge which surrounds the bottom inlet window.

* * * * *